US008690912B2

(12) United States Patent
Khanna et al.

(10) Patent No.: US 8,690,912 B2
(45) Date of Patent: *Apr. 8, 2014

(54) APPARATUS AND METHODS FOR FACILITATING HEMOSTASIS WITHIN A VASCULAR PUNCTURE

(71) Applicant: AccessClosure, Inc., Mountain View, CA (US)

(72) Inventors: Puneet K. Khanna, Rancho Mirage, CA (US); Farhad Khosravi, Los Altos Hills, CA (US)

(73) Assignee: AccessClosure, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/732,091

(22) Filed: Dec. 31, 2012

(65) Prior Publication Data

US 2013/0138147 A1   May 30, 2013

Related U.S. Application Data

(63) Continuation of application No. 10/928,744, filed on Aug. 27, 2004, now Pat. No. 8,348,971.

(51) Int. Cl.
*A61B 17/08*   (2006.01)

(52) U.S. Cl.
USPC ........................................ 606/213; 606/232

(58) Field of Classification Search
USPC ........................... 606/213–218, 232; 424/445
See application file for complete search history.

(56) References Cited

U.S. PATENT DOCUMENTS

| 5,312,642 | A  | * | 5/1994 | Chesterfield et al. | ........ 427/2.31 |
| 5,342,393 | A  | * | 8/1994 | Stack | ............... 606/213 |
| 2003/0088271 | A1 | * | 5/2003 | Cragg et al. | .................. 606/213 |
| 2005/0169974 | A1 | * | 8/2005 | Tenerz et al. | ................. 424/445 |

* cited by examiner

*Primary Examiner* — Gregory Anderson
(74) *Attorney, Agent, or Firm* — William A. English; Vista IP Law Group LLP (57) ABSTRACT

Apparatus for sealing a puncture communicating with a blood vessel includes a bioabsorbable sealing member secured to one end of a filament or other retaining member. The sealing member is delivered through the puncture into the vessel, and refracted against the wall of the vessel to provide temporary hemostasis. The sealing member is rapidly absorbed after exposure within the vessel, e.g., to an aqueous or heated physiological environment (e.g., exposure to blood or body temperature), immediately or shortly after completing a medical procedure via the puncture, e.g., within the time period that the patient is ambulatory. Optionally, extravascular sealing material is delivered into the puncture proximal to the sealing member. The retaining member and/or extravascular material may be bioabsorbable, being absorbed at a slower rate than the sealing member. Alternatively, the filament is removed from the puncture after hemostasis is established.

27 Claims, 6 Drawing Sheets

FIG. 6

APPARATUS AND METHODS FOR FACILITATING HEMOSTASIS WITHIN A VASCULAR PUNCTURE

RELATED APPLICATION DATA

This application is a continuation of application Ser. No. 10/928,744, filed Aug. 27, 2004, issuing as U.S. Pat. No. 8,348,971, the entire disclosure of which is expressly incorporated by reference herein.

FIELD OF THE INVENTION

The present invention relates generally to apparatus and methods for sealing punctures in a body, and more particularly, to apparatus and methods for sealing a vascular puncture extending through tissue into a blood vessel, and to apparatus and methods for delivering a fast-dissolving sealing device into a puncture extending from a patient's skin to a blood vessel or other body lumen to provide temporary hemostasis.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various apparatus and methods have been suggested for sealing a percutaneous puncture instead of using external pressure. For example, U.S. Pat. No. 5,108,421 issued to Fowler discloses a plug that may be delivered into a puncture through tissue. In one embodiment, a catheter is inserted through the puncture into the blood vessel. A balloon on the catheter is expanded and retracted until the balloon is disposed adjacent the puncture at the wall of the vessel. The plug may be advanced into the puncture until the plug contacts the balloon. Once the plug is positioned within the puncture, the balloon may be deflated and withdrawn, leaving the plug therein to expand and seal the puncture and/or to promote hemostasis.

Alternatively, U.S. Pat. No. 5,222,974 issued to Kensey et al. describes a system and method for sealing a percutaneous puncture in an artery. The system includes a sealing member including a resorbable plug, a rigid resorbable anchor member, and resorbable positioning member in the form of a filament. The disclosed sealing member is designed to resorb completely, e.g., within sixty to ninety (60-90) days.

U.S. Pat. No. 6,663,655 issued to Ginn et al. discloses a two-piece plug device for sealing a passage through tissue. The device includes a plug member and a sealing member disposed within a lumen of the plug member. The device is delivered into a puncture proximate to a vessel communicating with the puncture. The plug member and sealing member are made of a bioabsorbable material and may remain within the body until both components are absorbed.

U.S. Pat. No. 5,916,236 issued to Muijs Van de Moer et al. discloses an occlusion assembly that includes a flexible sheet attached to one end of a thread, and a retaining ring slidable along the thread towards the sheet. The sheet is folded, delivered via a sheath through a puncture into a blood vessel, and allowed to unfold within the vessel. The thread is pulled to direct the sheet against the wall of the vessel, whereupon the retaining ring is advanced down the thread to secure the sheet against the wall. The sheet, thread, and retaining ring are made of bioabsorbable material such that they disappear after a few weeks.

U.S. Pat. No. 4,890,612 issued to Kensey discloses a three-component closure device that includes a holding member or toggle, a filament, and a cylindrical plug made of bioabsorbable materials that is absorbed in approximately, forty five days, ninety days, and ten days, respectively. The closure device is delivered through a puncture into a blood vessel via a sheath, whereupon the filament is retracted to pull the toggle against the wall of the vessel with the plug within the puncture. The closure device remains in place until absorbed by the patient's body.

One of the disadvantages with these closure devices is that it may be difficult to position them properly with respect to the vessel, which may be significant since it is generally undesirable to expose collagen material to the bloodstream where it may float downstream and cause an embolism. In addition, these closure devices take a relatively long period of time to resorb and/or dissolve within the body (i.e., ten days or more). This is particularly undesirable for the portion of the device that is disposed within the blood vessel, because of the risk of a piece of the closure device breaking free and causing an embolism or other damage downstream of the puncture site.

Even when non-collagen materials are used for the portion of a closure device residing within a blood vessel, however, it may be desirable to minimize the amount of time the intravascular portion of the device is present within the vessel. Of course, if the device is absorbed too rapidly, it may adversely affect effective hemostasis of the puncture without risk of hematoma or other complications.

SUMMARY OF THE INVENTION

The present invention is directed to apparatus and methods for providing temporary or permanent hemostasis within a puncture extending through tissue, e.g., to a blood vessel or other body lumen, and/or to apparatus and methods for delivering a sealing device through a percutaneous puncture into a vessel or other body lumen that includes an intravascular component that is substantially absorbed during or shortly upon completing a procedure via the puncture.

In accordance with one embodiment, a device for sealing a puncture extending through tissue into a body lumen includes a filament or other elongate member, and a sealing member on a distal end of the elongate member formed from a bioabsorbable material that may be substantially absorbed by the body within not more than about twenty four (24) hours of exposure to an aqueous physiological environment, e.g., to blood or other fluid within the body lumen. In other embodiments, the sealing member may be substantially absorbed within not more than about twelve (12) hours, three (3) hours, one (1) hour, or even within not more than about thirty (30) minutes of exposure to an aqueous physiological environment within the body lumen. The retaining member may be formed from either a bioabsorbable or non-bioabsorbable material. Optionally, the device may also include extravascular sealing material deliverable within the puncture around the elongate member, e.g., a plug, a bolus of liquid sealing material, and the like.

In another embodiment, a device for sealing a puncture extending through tissue to a body lumen includes a filament or other elongate member formed from a first material, a sealing member formed from a second bioabsorbable material on a distal end of the elongate member, and extravascular sealing material formed from a third bioabsorbable material, the extravascular material being deliverable into the puncture around the elongate member. In one embodiment, the second bioabsorbable material may be absorbed at a faster rate compared to the third bioabsorbable material when exposed to an aqueous physiological environment, e.g., to blood or other fluid from the body lumen. Optionally, the first material is also bioabsorbable, e.g., at a slower rate compared to the second bioabsorbable material when exposed to an aqueous physiological environment.

In yet another embodiment, a method for sealing a puncture extending from a patient's skin through tissue to a body lumen includes delivering a sealing member into the body lumen, the sealing member formed from bioabsorbable material, retracting the sealing member against a wall of the body lumen, e.g., using a filament or other retaining member secured to the sealing member, to substantially seal the puncture from the body lumen. The sealing member may remain within the body lumen until it is substantially absorbed, e.g., within not more than about twenty-four hours of exposure to an aqueous physiological environment inside the blood vessel.

In one embodiment, the retaining member may be withdrawn from the puncture after the sealing member is absorbed, e.g., if the retaining member is formed from a non-bioabsorbable material. Alternatively, the retaining member may also be bioabsorbable, and may remain within the puncture until absorbed by the patient's body.

Optionally, sealing material, e.g., a plug and/or a single or multiple liquid sealing material, may be delivered into the puncture, e.g., around the retaining member, to further enhance hemostasis within the puncture. The sealing material may also be bioabsorbable, e.g., over a relatively longer time than the sealing member disposed within the body lumen.

Other aspects and features of the present invention will become apparent from consideration of the following description taken in conjunction with the accompanying drawings.

DETAILED DESCRIPTION OF THE PREFERRED EMBODIMENTS

Figure 1:
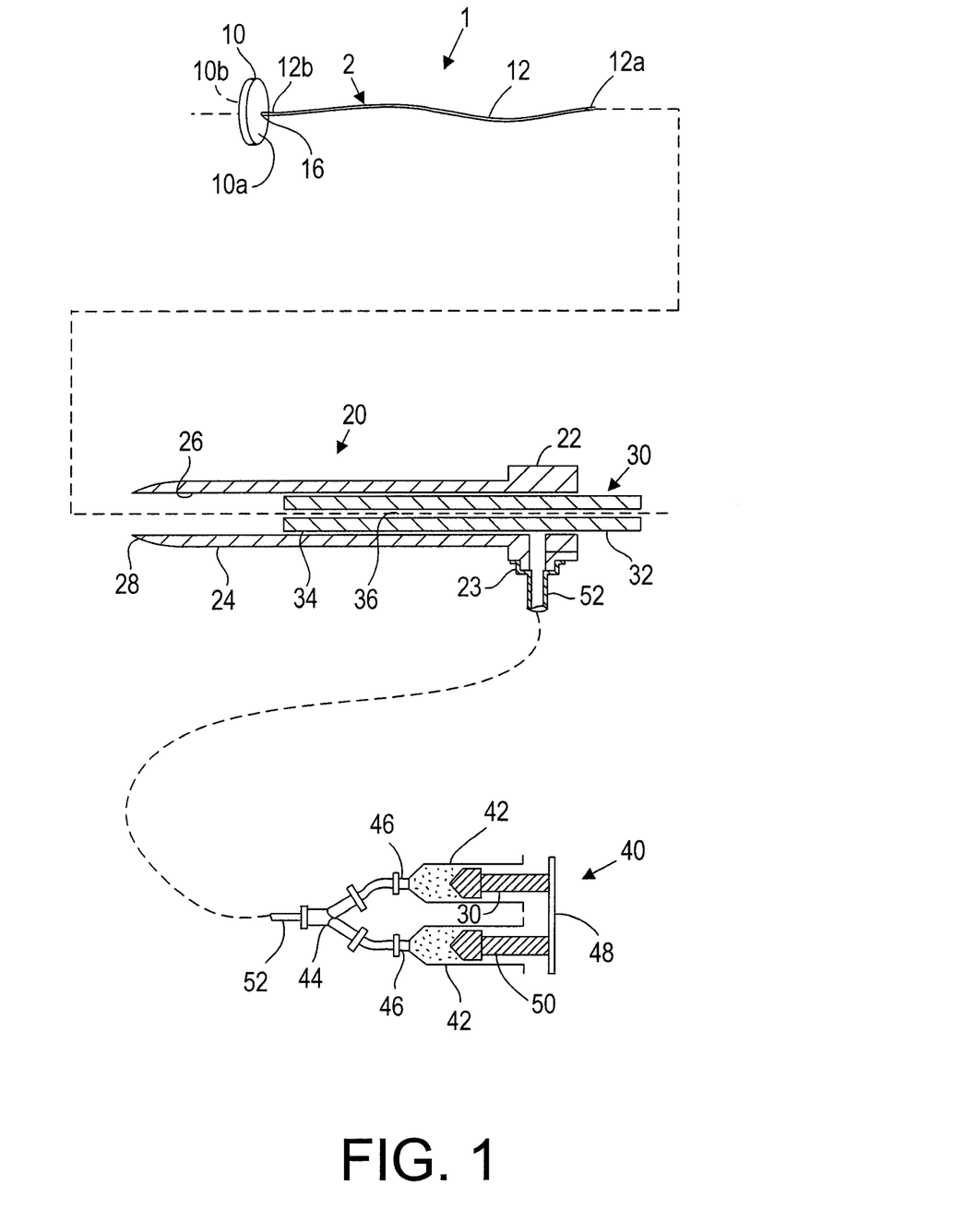
FIG. 1 is an exploded side view of an embodiment of an apparatus for facilitating hemostasis of a puncture extending through tissue.

Turning to the drawings, FIG. 1 illustrates an exemplary embodiment of a closure device 2 and an apparatus 1 for facilitating temporary or permanent hemostasis of a puncture extending through tissue using the closure device 2. Generally, the apparatus 1 includes a delivery sheath 20, and a plunger, catheter, or other pusher member 30 for deploying the closure device 2 from the delivery sheath 20. Optionally, the apparatus 1 may include a source of sealing material 40, e.g., that may be delivered via the delivery sheath 20, as described further below.

The closure device 2 generally includes a filament or other retaining member 12 including a proximal end 12a and a distal end 12b, and a bioabsorbable sealing member 10 on the distal end 12b. The filament 12 may be a solid or hollow elongate body, e.g., a suture, string, wire, tube, and the like, e.g., having a diameter, thickness, or other cross-sectional dimension of not more than about 0.90 mm. In one embodiment, the filament 12 may be a bioabsorbable suture, e.g., made from poly(glycolic-co-lactic) acid, poly (glycolic acid), and the like. In this embodiment, the retaining member 12 may be made from material that may be absorbed over a longer period of time compared to the sealing member 10. For example, the filament 12 may be absorbed over a period of at least about twenty-four (24) hours after exposure to an aqueous environment, and may take as long as days, weeks, or even months to absorb completely. Alternatively, the filament 12 may be formed from a biocompatible, nonbioabsorbable material, such as nylon, Teflon, catgut, silk, polypropylene, and the like.

The filament 12 may be substantially flexible, i.e., having little or no column strength. Alternatively, the filament 12 may have sufficient column strength such that the distal end 12b carrying the sealing member 10 may be advanced distally, e.g., from the delivery sheath 20, by pushing on the proximal end 12a of the filament 12, as described further below. The filament 12 should have sufficient strength in tension to allow the sealing member 10 to be pulled through a puncture against a wall of a blood vessel or other body lumen, e.g., to substantially seal the puncture from the vessel without the filament 12 breaking and/or separating from the sealing member 10.

Optionally, particularly if the filament 12 is not bioabsorbable, an exterior surface of the filament 12 may include a lubricious coating or other material, for example, to facilitate withdrawing the filament 12 through a puncture, e.g., after the puncture has been at least partially filled with sealing material around the filament 12, as explained further below.

As shown, the sealing member 10 is affixed to the distal end 12b of the filament 12 at a fixation or toggle location 16, e.g., at or near the center or midpoint of the sealing member 10.

The filament 12 may be at least partially embedded within the sealing member 10 at the fixation location 16 and/or may extend at least partially around to secure the sealing member 10 to the distal end 12b. For example, the distal end 12b may include a loop (not shown) that may be secured around a portion of the sealing member 10 and/or may extend through one or more openings (also not shown) through the sealing member 10. In addition or alternatively, an adhesive or other material (not shown) may be used to attach the distal end 12b to the sealing member 10.

The sealing member 10 may be a body generally defining a plane, i.e., having a thickness or other minor dimension that is substantially smaller than its width, diameter, or other major dimension. For example, as shown, the sealing member 10 may be generally disk-shaped, having a circular, square, polygonal, or other shape generally within a plane and defining upper and lower surfaces 10a, 10b. The generally upper and lower surfaces 10a, 10b may be substantially planar, concave and/or convex (not shown).

The sealing member 10 may be formed from a rapidly absorbing, biocompatible material. As used herein, "rapidly absorbing" means material that is absorbed by any physical process (e.g., dissolving, melting, or the like) within a relatively short period of time, e.g., not more than about twenty four (24) hours, e.g., upon exposure to an aqueous physiological environment. An example of an aqueous physiological environment is a location within a patient's body exposed to blood or other bodily fluids, such as an interior of a blood vessel or other organ.

In other embodiments, the sealing member 10 may be substantially absorbed within about twelve (12) hours of exposure to an aqueous physiological environment, within about three (3) hours, about one (1) hour, or even less than about thirty (30) minutes of exposure to an aqueous physiological environment. In this regard, the intravascular aspect of the closure device 2, namely, the sealing member 10, may be substantially absorbed before the patient becomes ambulatory, i.e., during or immediately following a procedure performed via the puncture. Thus, the amount of time that the sealing member 10 remains intact within the patient's body may be minimized compared to known closure devices that may be absorbed by a patient's body over days, weeks, or months.

Exemplary materials for the sealing member 10 may include carbohydrate (sugar) or salt-based materials, e.g., that rapidly dissolve in the presence of an aqueous environment, e.g., blood or other bodily fluids. In addition or alternatively, the sealing member 10 may be formed from a material that rapidly melts due to the increased temperature within a patient's body, e.g., when exposed to temperatures of about thirty seven degrees Celsius (37° C.) or more.

In one embodiment, the sealing member 10 may be preformed into a shape that prevents the sealing member 10 from being pulled easily through an arteriotomy or other opening through a wall of a blood vessel or other body lumen into a puncture (not shown). Further, the shape of the sealing member 10 may aid in substantially sealing such a puncture from the vessel, e.g., to provide temporary hemostasis. Optionally, the sealing member 10 may include structural features (e.g., structural reinforcement elements, shaped sealing surfaces, and the like, not shown) that may aid in preventing the sealing member 10 from being dislodged through an arteriotomy or other opening once deployed.

The sealing member 10 may be substantially rigid, i.e., fixed in a shape, such as an elongate foot, plate, sheet, a generally disk-shape, or other configuration. Alternatively, the sealing member 10 may be semi-rigid, i.e., such that the shape of the sealing member 10 may conform at least partially to contacted anatomy, e.g., assuming a curved shape conforming to a wall of a vessel or other body lumen when directed against the wall.

In a further alternative, the sealing member 10 may be substantially flexible, i.e., capable of being deformed into a contracted condition, e.g., to facilitate loading within the delivery sheath 20, and expandable into an enlarged condition, e.g., a generally disk-shaped configuration, when deployed from the delivery sheath 20 and/or when free from outside stresses. For example, the sealing member 10 may be rolled into a generally tubular shape to facilitate loading into the delivery sheath 20, may be compressed or deflected into a lower profile contracted condition, and the like.

With continued reference to FIG. 1, the delivery sheath 20 may be a substantially rigid, semi-rigid, and/or flexible tubular body, including a proximal end 22, a distal end 24 having a size and shape for insertion into a puncture, and a lumen 26 extending therebetween. The distal end 24 may be tapered and/or may include a substantially atraumatic tip 28 to facilitate advancement through a puncture. The delivery sheath 20 may include a handle (not shown), and/or one or more seals, e.g., a hemostatic seal (also not shown), on the proximal end 22. The closure device 2 may be carried by the delivery sheath 20 such that the sealing member 10 is disposed within the lumen 26 proximate to the distal end 24. The lumen 26 may be sized such that the closure device 2 is slidable therein, e.g., able to traverse distally from the delivery sheath 20 during delivery, as described further below. Optionally, the delivery sheath 20 may include a lubricious coating or other material (not shown) to facilitate sliding the sealing member 10 along the lumen 26, e.g., during deployment.

The pusher member 30 may be an elongate member, e.g., a plunger, catheter, and the like, including a proximal end 32, and a distal end 34 having a size for slidable insertion into and/or movement within the lumen 26 of the delivery sheath 20. The distal end 34 of the pusher member 30 may be substantially blunt or otherwise shaped to facilitate contacting and/or pushing the sealing member 10 within the delivery sheath 20, as described further below. The pusher member 30 may be substantially rigid, semi-rigid, and/or substantially flexible, having sufficient column strength to allow movement of the delivery sheath 20 relative to the sealing member 10 without buckling. The pusher member 30 may also include a lumen 36 extending between the proximal end and the distal end 34, e.g., to accommodate the filament 12 of the closure device 2 and/or a guidewire (not shown) therethrough.

Optionally, as shown in FIG. 1, the apparatus 1 may include a source of sealing material, e.g., syringe assembly 40, for delivering liquid hydrogel precursors or other sealing material 99 into a puncture, e.g., to provide an extravascular sealing component in addition to the intravascular sealing member 10. In one embodiment, the syringe assembly 40 may include a pair of syringes 42 that include two components of a sealing compound therein, a "Y" fitting 44 connected to outlets 46 of the syringes 42, and tubing 52 connectable between the "Y" fitting 44 and a side port 23 on the proximal end 22 of the delivery sheath 20. A plunger assembly 48 may be slidable into the syringes 42 to cause the components therein to be delivered through the outlets 46.

In one embodiment, the plunger assembly 48 may include a pair of plungers 50 that are coupled to one another yet are received in respective syringes 42. Thus, both plungers 50 may be manually depressed substantially simultaneously to deliver the components in the syringes 42 out together. Alternatively, an auto-injection device may be provided for delivering the components from the syringes 42, such as that disclosed in co-pending application Ser. No. 10/806,952, filed Mar. 22, 2004, the entire disclosure of which is expressly incorporated herein by reference.

In one embodiment, a liquid precursor polymer compound is provided in each syringe 42 of the syringe assembly 40 that, when mixed together, may be activated to form a hydrogel, such as a poly(ethylene glycol)-based (PEG) multiple component hydrogel. Additional information on hydrogels and systems for delivering them are disclosed in U.S. Pat. Nos. 6,152,943, 6,165,201, 6,179,862, 6,514,534, 6,379,373, and 6,703,047, and in co-pending application Ser. No. 09/776,120 filed Feb. 2, 2001, Ser. No. 10/010,715 filed Nov. 9, 2001 published as U.S. Patent Application Publication No. 2003-0012734 A1, and Ser. No. 10/068,807 filed Feb. 5, 2002 published as U.S. Patent Application Publication No. 2002-0114775 A1. The disclosures of these references and any others cited therein are expressly incorporated by reference herein.

Figure 4:
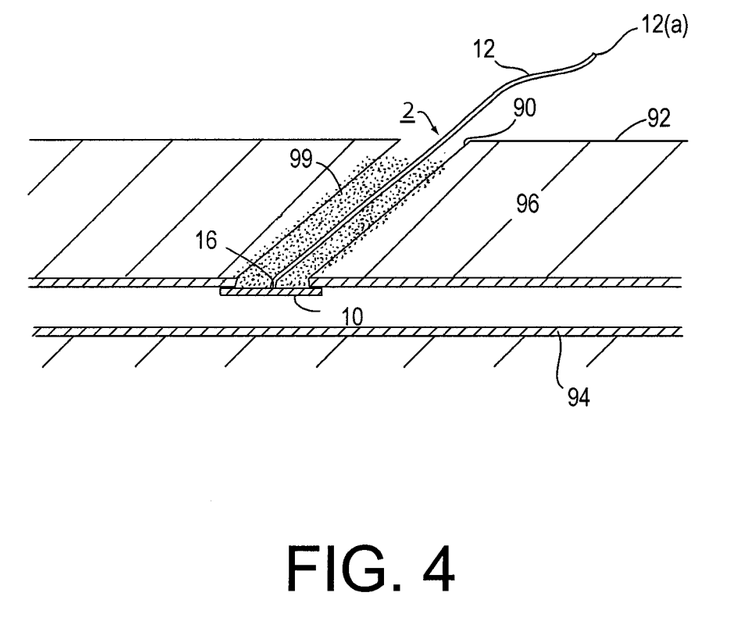
FIG. 4 is a cross-sectional view of a patient's body, showing a system for sealing a puncture extending through tissue to a blood vessel that includes an intravascular and extravascular sealing components.

As shown in FIG. 4, the extravascular sealing material 99 may be delivered into a puncture 90 around the filament 12. If the filament 12 is bioabsorbable, the sealing material 99 may at least partially adhere to the filament 12, e.g., to enhance securing the sealing member 10 against the wall of the vessel 94, as described further below. Alternatively, if the filament 12 is to be removed, an exterior surface of the filament 12 may include a lubricious coating or other coating to facilitate pulling the filament 12 through the sealing material 99.

The sealing material 99 may be formed from other bioabsorbable and/or biocompatible material. Similar to the filament 12, the sealing material 99 may be absorbed over a longer period of time compared to the sealing member 10. In exemplary embodiments, the sealing material 99 may be absorbed over a period of time of not less than about twenty-four (24) hours after exposure to an aqueous environment, e.g., in not less than about seven to fourteen (7-14) days.

For example, the sealing material 99 may be formed from biologic-based material, such as collagen, fibrin, carboxymethylcellulose, oxidized cellulose, alginates, gelatin, or other protein-based material, and/or synthetic materials, such as polyglycolic acids (PGA's), polyactides (PLA's), and the like. The sealing material 99 may be formed into a discernable structure such as a plug, and the like.

Figure 2A:
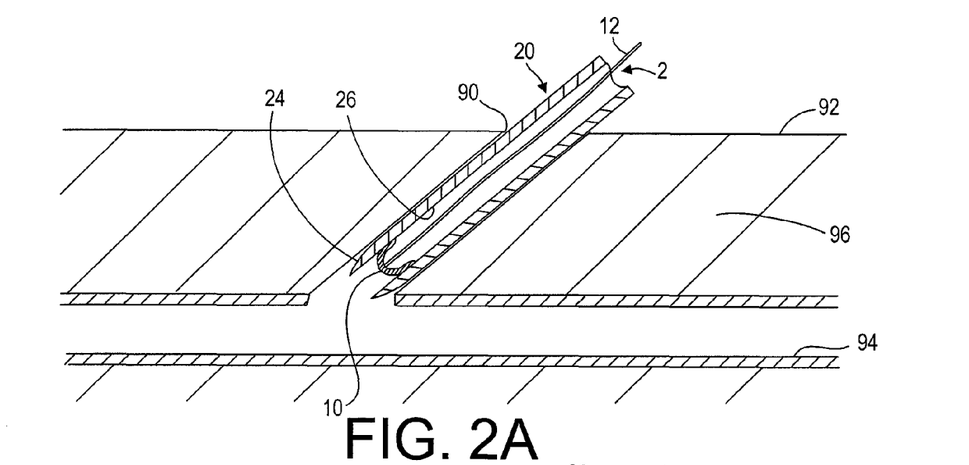
FIGS. 2A-2C are cross-sectional views of a patient's body, showing a method for sealing a puncture extending through tissue to a blood vessel.
Figure 2B:
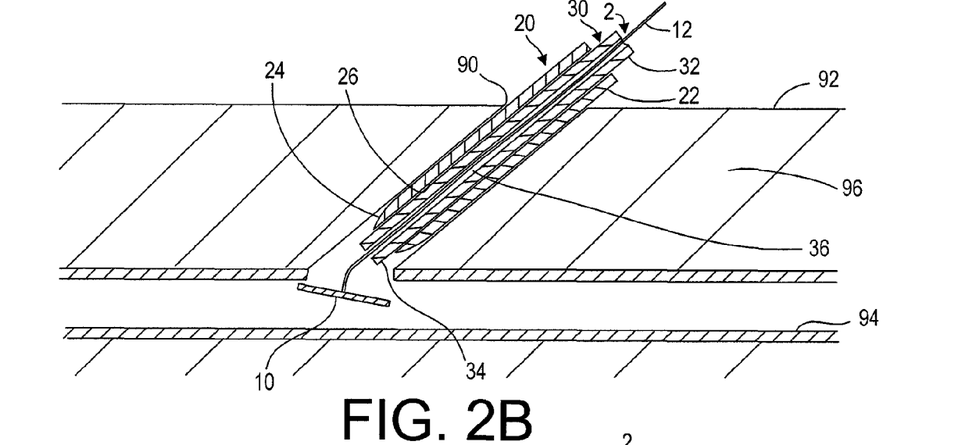
Figure 2C:
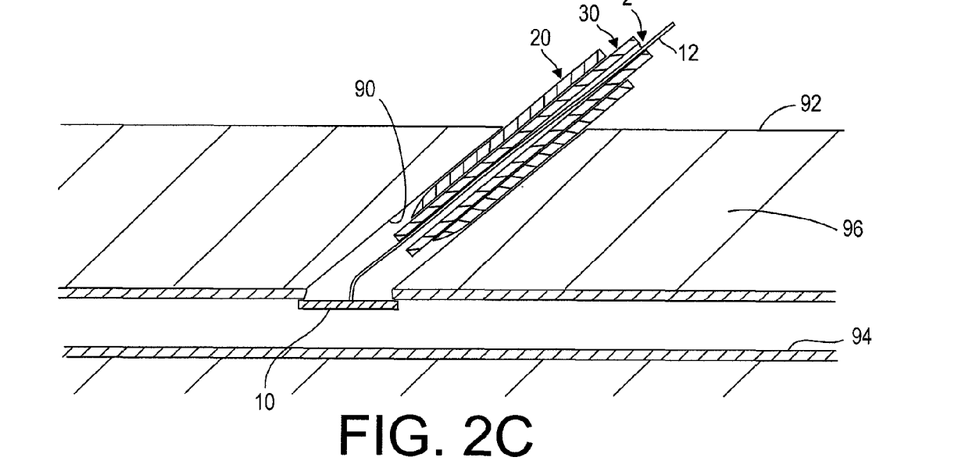

Turning to FIGS. 2A-2C, an exemplary method is shown for delivering a sealing device, such as the closure device 2 described above, into a puncture 90 extending through tissue 96 and to a blood vessel or other body lumen 94. Generally, the puncture 90 extends from a patient's skin 92 through intervening tissue 96, e.g., to a body lumen 94. In an exemplary embodiment, the puncture 90 may be a percutaneous puncture communicating with a blood vessel 94, such as a femoral artery, carotid artery, and the like.

In an exemplary method, the puncture 90 may be created using known procedures, e.g., using a needle, guidewire, one or more dilators, and the like (not shown). An introducer sheath (also not shown) may be advanced through the puncture 90 into the vessel 94, e.g., to provide access into the vessel 90 for one or more instruments, and/or allow one or more diagnostic and/or interventional procedures to be performed via the vessel 90, as is known in the art. Upon completing the procedure(s) via the vessel 94, any instruments and/or the introducer sheath (not shown) may be removed from the puncture 90.

Turning to FIG. 2A, an embodiment of the apparatus 1 is shown in which a sealing member 10 of a closure device 2 is loaded into a lumen 26 of a delivery sheath 20 in a contracted condition. In FIG. 2A, the pusher member 30 (described above and shown in FIG. 1) has been omitted for convenience.

As shown, the sealing member 10 may have its outer edges folded inwardly to reduce the profile of the sealing member, and the outer edges may be constrained within the delivery sheath 20. The pusher member 30 may be disposed within the lumen 26 with its distal end 34 adjacent the sealing member 10. The apparatus 1 may be inserted into the puncture 90 and advanced distally until the distal end 24 of the delivery sheath 20 is disposed adjacent the vessel 94 or even enters the vessel 94.

Turning to FIG. 2B, the pusher member 30 may be advanced distally, e.g., while maintaining the delivery sheath 20 substantially stationary with the distal end 24 within the vessel 90, to deploy the sealing member 10 within the vessel 94. As shown, when the sealing member 10 exits from the distal end 24 of the delivery sheath 20, the sealing member 10 may resiliently return from the contracted condition towards an enlarged condition, e.g., in the shape of a generally planar disk, plate, sheet, or other relaxed state.

Alternatively, if the filament 12 is pushable from the proximal end 12a (i.e., having sufficient column strength), the proximal end 12a of the filament 12 may be directed distally into the delivery sheath 20 to advance the distal end 12b and the sealing member 10 out of the delivery sheath 20 into the vessel 94. In this alternative, it may be possible to eliminate the pusher member 30 completely. In addition, the delivery sheath 20 may include a lubricious coating or other material (not shown) to facilitate sliding the sealing member 10 out of the distal end 24 of the delivery sheath 20.

Turning to FIG. 2C, the filament 12 may then be drawn proximally to retract the closure device 2 at least partially through the puncture 90, e.g., until the sealing member 10 is directed into contact with the wall of the vessel 94. The delivery sheath 20 may also be at least partially retracted, e.g., if the distal end 24 is advanced into the vessel 94 before or during deployment of the sealing member 10.

Figure 3A:
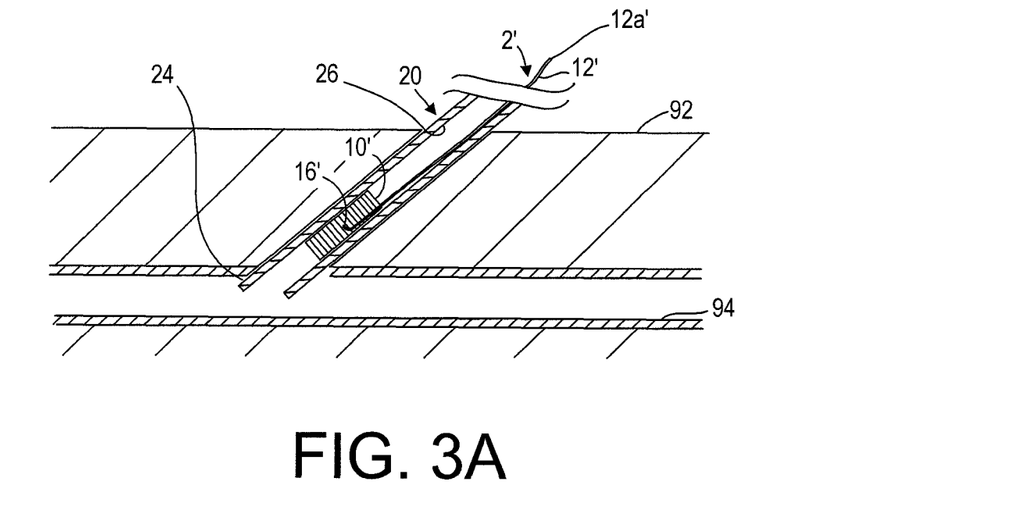
FIGS. 3A and 3B are cross-sectional views of a patient's body, showing another apparatus and method for sealing a puncture extending through tissue to a blood vessel.
Figure 3B:
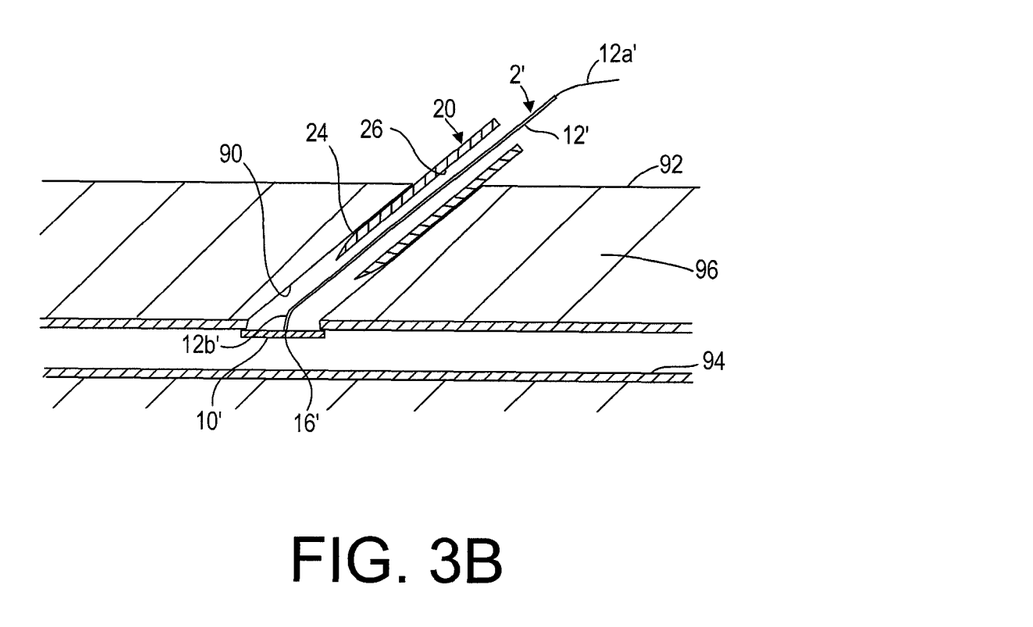

Turning to FIGS. 3A and 3B, in another embodiment, the closure device 2' may include a filament or other retaining member 12' including a proximal end 12a' and a distal end 12b,' and a sealing member 10' attached to the distal end 12b' to provide a toggle-type device. In this embodiment, the filament 12' may be secured to the sealing member 10' at a fixation location 16,' e.g., located in the middle or center of the sealing member 10.' The sealing member 10' may be disposed within the delivery sheath 20 such that its longitudinal axis or major dimension is disposed axially within the lumen 26 of the delivery sheath 20, as shown in FIG. 3A.

When the toggle-type sealing member 10' is deployed from the delivery sheath 20 and/or within the vessel 94, the sealing member 10 may orient itself within the blood vessel 94 with its longitudinal axis or major dimension disposed transversely to the longitudinal axis of the delivery sheath 20, e.g., along a length of the vessel 94, as shown in FIG. 3B. The sealing member 10' may then be directed against the wall of the vessel 94 by pulling the filament 12' proximally from the puncture 90. Although a width or minor dimension of the sealing member 10' may be less than a width of the arteriotomy or other opening in the wall of the vessel 94, the sealing member 10' may facilitate hemostasis. For example, the sealing member 10' may compress the wall of the vessel 94 and/or otherwise at least partially occlude the opening to substantially seal the puncture 90 from the vessel 94.

Figure 5:
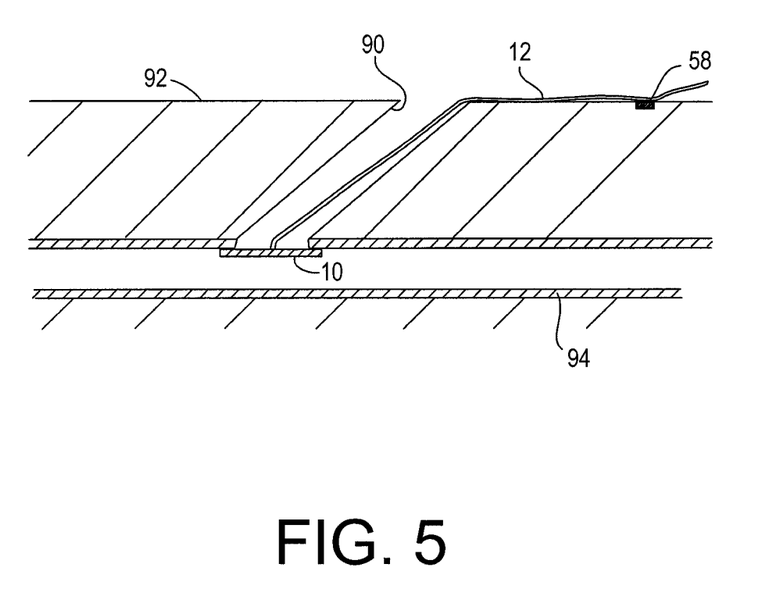
FIG. 5 is a cross-sectional view of a patient's body, showing yet another device and method for sealing a puncture extending through tissue to a blood vessel.

Turning to FIG. 5, in one embodiment, the sealing member 10 (or alternatively another sealing member, such as the sealing member 10' of FIG. 3B) may be retained against the wall of the vessel 94, e.g., to substantially seal the puncture 90 from the vessel 94. Thus, the sealing member 10 may enhance hemostasis, preventing blood or other fluid within the vessel 94 from leaking into the puncture 90. The sealing member 10 may be absorbed after sufficient time for the tissue 96 surrounding the puncture 90 may at least partially occlude the puncture 90, e.g., by coagulation of blood or other mechanisms.

Optionally, external pressure may be applied to the patient's skin 92 above the puncture 90 to further enhance hemostasis. In addition or alternatively, the proximal end 12a of the filament 12 may be secured relative to the patient, e.g., by taping, strapping, adhering, or otherwise securing the proximal end 12a to the patient's skin 92 adjacent the puncture 90 at 58, as shown in FIG. 5. The proximal end 12a may be secured at a location that ensures that the filament 12 remains under sufficient tension to maintain the sealing member 10 in place against the wall of the vessel 94, e.g., to substantially seal the puncture 90 from the vessel 94.

Figure 6:
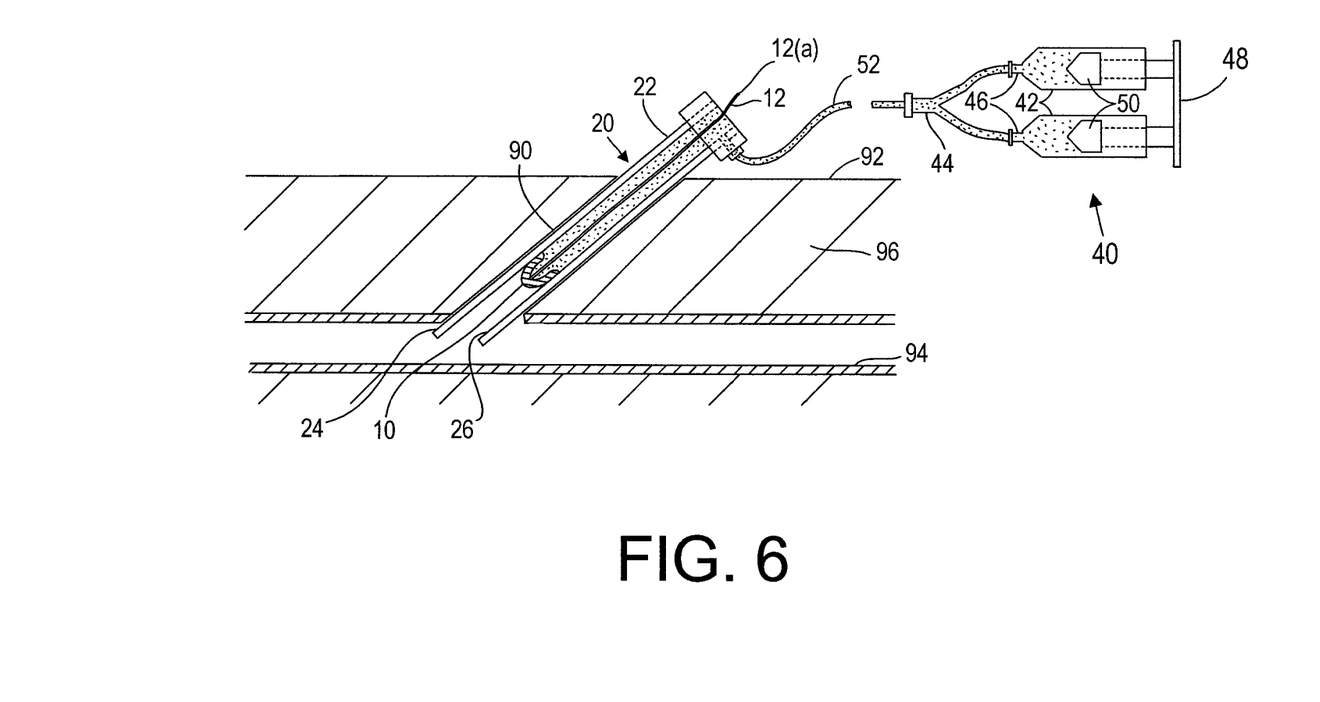
FIG. 6 is a cross-sectional view of a patient's body, showing still another embodiment of an apparatus and method for sealing a puncture extending through tissue to a blood vessel.

Alternatively, as shown in FIG. 6, the delivery device 20 may be used to deliver sealing material 99 into the puncture proximal to the sealing member 10. As described above with reference to FIG. 1, the delivery sheath 20 may include a side port 23 coupled to tubing 52 which, in turn, is coupled to syringe assembly 40. The side port 23 may communicate with the lumen 26 of the delivery sheath 20 such that, when two hydrogel precursors within the syringes 42 are directed out the outlets 46, they mix in the "Y" fitting 44, initiating the hydrogel reaction, and pass through the tubing 52, side port 23, lumen 26, and out the distal end 24 of the delivery sheath 20 into the puncture 90.

Optionally, the delivery sheath 20 may be withdrawn proximally as the sealing material 99 is delivered, e.g., to fill the puncture 90. Alternatively, the delivery sheath 20 may not include a side port, and a separate injection sheath (not shown) may be used to deliver the sealing material 99. In this alternative, the delivery sheath 20 may be removed after delivering the sealing member 10, and the injection sheath may be advanced over the filament 12 into the puncture 90 to deliver the sealing material, similar to the methods described elsewhere herein.

In another alternative, injection of the hydrogel precursor mixture into the lumen 26 of the delivery sheath 20 may be used to force the sealing member 10 out of the lumen 20, i.e., to initially deploy the sealing member 10 into the vessel 94. After the sealing member 10 has been ejected from the delivery sheath 20 into the vessel 94 in this manner, further hydrogel precursor mixture delivery may be discontinued, until the sealing member 10 is retracted against the wall of the vessel 94.

In further alternatives, the pusher member 30 may be used to deliver the sealing material 99 into the puncture, e.g., via lumen 36, similar to the methods described above.

Once the sealing member 10 has been deployed within the vessel 94, the sealing member 10 may begin to be absorbed rapidly, e.g., due to exposure to blood within the vessel 94. As explained above, the sealing member 10 may dissolve within not more than about twenty-four (24) hours after deployment. In one embodiment, the filament 12 may also be formed from bioabsorbable material, although the filament material may be absorbed over a longer period of time, e.g., greater than about twenty-four (24) hours after exposure within the patient's body. Similarly, the extravascular sealing material 99 may also be bioabsorbable, e.g., at a rate substantially slower than the sealing member 10.

In an alternative embodiment of the invention, if the filament is not bioabsorbable, the filament 12 may be removed, e.g., by pulling the filament 12 out of the patient's body after sufficient time for the sealing member 10 to dissolve. For example, the proximal end 12a may be released, if secured to the patient's skin 92, and pulled through the extravascular sealing material 99 and out of the puncture 90. Thus, the filament 12 may remain until hemostasis has been substantially established and/or after the sealing member 10 has been substantially absorbed. In this regard, the filament 12 may be removed at the time of patient ambulation, e.g., before discharge from the medical facility, or even subsequently during a follow-up visit. In this embodiment, the filament 12 may have a sufficiently small diameter or other cross-section so that the small tract resulting from its removal does not bleed or otherwise leak substantially. Any bleeding or leaking may be managed, e.g., by compression for a short period of time or a compressive bandage (not shown).

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

We claim:

1. A device for sealing a puncture extending through tissue to a body lumen, comprising:
    an elongate retaining member comprising a proximal end and a distal end sufficiently small to be directed through the puncture; and
    a sealing member on the distal end of the retaining member, the sealing member formed entirely from bioabsorbable material that is substantially absorbed within not more than about twenty-four hours of exposure to an aqueous physiological environment within the body lumen.

2. The device of claim 1, wherein the retaining member is substantially absorbed after at least about twenty-four hours of exposure within the body lumen.

3. The device of claim 1, wherein the retaining member comprises non-bioabsorbable material and a lubricious material on an exterior surface of the retaining member.

4. The device of claim 1, wherein the sealing member is compressible from a generally planar enlarged condition to a contracted condition to facilitate delivery of the sealing member through the puncture into the body lumen.

5. The device of claim 4, wherein the sealing member is biased to assume the enlarged condition when released within the body lumen, the enlarged condition defining a cross-section preventing the sealing member from being withdrawn from the body lumen into the puncture.

6. An apparatus device for sealing a puncture extending through tissue into a blood vessel, comprising:
    a tubular member comprising a proximal end, a distal end having a size and shape for insertion into the puncture, and a lumen extending between the proximal and distal ends;
    a closure device comprising a sealing member and an elongate retaining member, the sealing member formed entirely from a first bioabsorbable material disposed within the lumen of the tubular member, the retaining member comprising a proximal end extending proximally through the lumen to the proximal end of the tubular member, a distal end coupled to the sealing member, and a lubricious material on an exterior surface of the retaining member, and
    an extravascular sealing material deliverable into the puncture around the retaining member, the extravascular sealing material comprising a second bioabsorbable material that is absorbed at a different rate than the first bioabsorbable material when exposed to an aqueous physiological environment.

7. The apparatus of claim 6, wherein the retaining member comprises a third bioabsorbable material that is absorbed at a slower rate than the first bioabsorbable material when exposed to an aqueous physiological environment.

8. The apparatus of claim 7, wherein the third bioabsorbable material is substantially absorbed after at least about twenty-four hours of exposure within the body lumen.

9. The apparatus of claim 6, wherein the retaining member comprises non-bioabsorbable material.

10. The apparatus of claim 6, wherein the sealing member comprises at least one of a carbohydrate and a salt that is substantially absorbed within about twenty-four hours of exposure to an aqueous physiological environment within the body lumen.

11. The apparatus of claim 6, wherein the sealing member is biased to assume the enlarged condition when released within the body lumen, the enlarged condition defining a cross-section preventing the sealing member from being withdrawn from the body lumen into the puncture.

12. The apparatus of claim 6, wherein the extravascular material comprises a solid plug deliverable into the puncture.

13. The apparatus of claim 6, further comprising a pusher member disposed within the lumen of the tubular member proximal to the sealing member, the pusher member being slidable axially relative to the tubular member for deploying the sealing member from the lumen beyond the distal end of the tubular member.

14. The apparatus of claim 6, wherein the second bioabsorbable material is absorbed at a slower rate than the first bioabsorbable material when exposed to an aqueous physiological environment.

15. The apparatus of claim 6, wherein the second bioabsorbable material is a protein-based material, and the first bioabsorbable material is a different material than the second bioabsorbable material.

16. The apparatus of claim 6, wherein the retaining member is formed from bioabsorbable material that is absorbed at a different rate than the sealing member when exposed to an aqueous physiological environment.

17. A method for sealing a puncture extending through tissue into a body lumen using a closure device, the closure device comprising a bioabsorbable sealing member on one end of a elongate retainer, the method comprising:
delivering the sealing member into the body lumen with the elongate retainer extending proximally into the puncture, the elongate retainer including a lubricious material on an exterior surface thereof;
retracting the elongate retainer to direct the sealing member against a wall of the body lumen;
advancing extravascular sealing material into the puncture around at least a portion of the elongate retainer; and
leaving the sealing member within the body lumen for a time period during which the entire sealing member is substantially absorbed within the body lumen, wherein the extravascular sealing material comprises bioabsorbable material that is absorbed at a different rate than the sealing member when exposed to an aqueous physiological environment.

18. The method of claim 17, wherein the extravascular sealing material comprises bioabsorbable material that is absorbed at a slower rate than the sealing member when exposed to an aqueous physiological environment.

19. The method of claim 17, wherein the extravascular sealing material comprises a plug device delivered into the puncture over the elongate retainer.

20. The method of claim 17, further comprising withdrawing the elongate retainer from the puncture after the sealing member is substantially absorbed within the body lumen.

21. The method of claim 17, wherein the elongate retainer comprises bioabsorbable material that is absorbed at a slower rate than the sealing member when exposed to an aqueous physiological environment, the method further comprising leaving the elongate retainer within the puncture until the elongate retainer is substantially absorbed.

22. The method of claim 17, further comprising securing a proximal end of the elongate retainer to a location to maintain the sealing member against the wall of the body lumen.

23. The method of claim 22, wherein the securing is carried out by one selected from the group consisting of taping, strapping, and adhering.

24. The method of claim 17, further comprising enlarging the sealing member prior to the retracting step.

25. The method of claim 17, further comprising toggling the sealing member prior to the retracting step.

26. The method of claim 17, further comprising pushing on the proximal end of the elongate retainer to advance the sealing member.

27. The method of claim 17, wherein the extravascular sealing material has a greater length than the sealing member when introduced into the puncture.

* * * * *